United States Patent [19]

Copar

[11] Patent Number: 5,310,898
[45] Date of Patent: May 10, 1994

[54] ALKYLENEDIAMMONIUM DICLAVULANATE DERIVATIVES, A PROCESS FOR THE PREPARATION THEREOF AS WELL AS THE USE THEREOF

[75] Inventor: Anton Copar, Smartno pri Litiji, Spratly Islands

[73] Assignee: LEK, tovarna farmacevtskih, Spratly Islands

[21] Appl. No.: 36,893

[22] Filed: Mar. 25, 1993

[30] Foreign Application Priority Data

Mar. 26, 1992 [AT] Austria .............................. A-619/92

[51] Int. Cl.[5] .................. A61K 31/42; C07D 498/047; C07B 63/02
[52] U.S. Cl. .................................................... 540/349
[58] Field of Search ......................................... 540/349

[56] References Cited

U.S. PATENT DOCUMENTS

| 4,454,069 | 6/1984 | Cook et al. | 540/349 |
| 4,525,353 | 6/1985 | Cole | 424/114 |
| 4,647,659 | 3/1987 | Cook et al. | 540/349 |
| 4,650,795 | 3/1987 | Liberman | 540/349 |

FOREIGN PATENT DOCUMENTS 2517316 10/1975 Fed. Rep. of Germany .

OTHER PUBLICATIONS

An Encyclopedia of Chemicals, Drugs, and Biologicals, The Merck Index, 11th Edition, 1989, Nos. 1072, 7037, 7047.

*Primary Examiner*—Mark L. Berch
*Attorney, Agent, or Firm*—Pollock, Vande Sande & Priddy

[57] ABSTRACT

A novel process for the preparation of calvulanic acid and pharmaceutically acceptable salt thereof, such as potassium clavulanate, is described. According to the novel process, crude clavulanic acid, which is present in the form of an extract in an organic solvent, such as ethyl acetate, the extract having been obtained in known manner upon fermentation with a calvulanic acid producing microorganism, is reacted with substituted alkylenediamines of the formula II

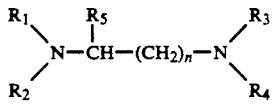

wherein the substituents $R_1$, $R_2$, $R_3$, $R_4$ and $R_5$ and n have the meanings as defined in claim 1, e.g. with N,N'-diisopropylethylenediamine, to the novel alkylenediammonium diclavulanates of the formula I

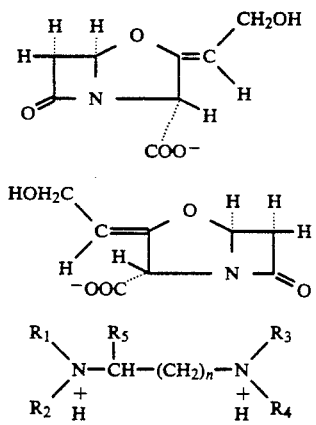

wherein the substituents $R_1$, $R_2$, $R_3$, $R_4$ and $R_5$ and n have the meanings as defined in claim 1, e.g. to N,N'-diisopropylethylenediammonium diclavulanate. The obtained compounds of the formula I are optionally isolated and converted with alkali alkanoates, such as potassium 2-ethylhexanoate in isopropanol, to potassium clavulanate.

Because of their high inhibitory action against beta-lactamases and because of a significant synergistic action in combination with the beta-lactam antibiotics from the group of penicillins and cephalosporins, clavulanic acid and pharmaceutically acceptable salts thereof are valuable compounds for the preparation of galenic compositions, which are active in the treatment of infectious diseases induced by numerous grampositive and gramnegative microorganisms.

4 Claims, No Drawings

ALKYLENEDIAMMONIUM DICLAVULANATE DERIVATIVES, A PROCESS FOR THE PREPARATION THEREOF AS WELL AS THE USE THEREOF

TECHNICAL FIELD

The present invention belongs to the field of pharmaceutical industry and relates to novel alkylenediammonium diclavulanate derivatives, to a process for the preparation thereof as well as to the use thereof as intermediate compounds for the preparation of clavulanic acid and of pharmaceutically acceptable alkali salts thereof, such as potassium clavulanate.

BACKGROUND PART

Clavulanic acid, (2R,5R,Z)-3-(2-hydroxyethylidene)-7-oxo-4-oxa-1-azabicyclo-[3,2,0]-heptane-2-carboxylic acid, is a known compound of the following structure:

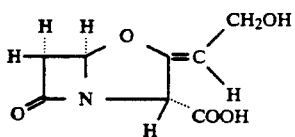

This compound as well as the salts and esters thereof are active as inhibitors of betalactamase, i.e. they inhibit beta-lactamases produced by gram-positive and gram-negative microorganisms. Hence clavulanic acid and its salts are used in gelenic preparations in order to inhibit the inactivation of beta-lactam antibiotics. Commercial preparations contain a stable potassium salt of clavulanic acid (clavulanic acid itself being rather unstable) in combination with amoxicillin trihydrate.

Clavulanic acid is obtained by a fermentation method from various microorganisms belonging to various Streptomycetes strains such as S. clavuligerus NRRL 3585, S. jumoninensis NRRL 5741, S. katsurahamanus IFO 13716 and Streptomyces sp. P 6621 FERM P2804.

Clavulanic acid and its salts were first disclosed in GB 1,508,977. However, the process for the preparation of clavulanic acid described therein is time-consuming and is based on exacting purifications by means of various chromatographic methods. The salts of clavulanic acid are obtained by binding the clavulanate anion present in the filtrate of the fermentation broth on an anionic exchange resin, subsequent elution of the clavulanate anion therefrom by means of an electrolyte, desalting the obtained eluate, passing the latter through another anionic exchange resin and a subsequent chromatographic elution therefrom by means of an electrolyte, repeatedly desalting the obtained eluate and removing the solvent.

The process requires the use of preparative chromatographic columns, which represents a considerable investment expenditure; in addition, the applicability on a large scale is limited.

A further drawback of this process is the fact that the most steps thereof are carried out in an aqueous medium where clavulanic acid is very unstable.

GB 1,543,563 discloses a modified fermentative process, wherein the pH value of the medium is maintained within the range from 6.3 to 6.7, which results in an increased yield of the desired compound. The salts of clavulanic acid such as potassium clavulanate are obtained from lithium clavulanate by double exchange.

According to the process for the preparation of clavulanic acid and of pharmaceutically acceptable salts thereof as disclosed in EP-0-026044, the exacting methods of purification by means of exchange resins are largely avoided. The process is based on the preparation of the tert. butylamine salt of clavulanic acid, preferably in the form of its acetone solvate. The tert. butylamine salt of clavulanic acid is prepared by treating the extract, preferably the ethyl acetate extract, containing crude clavulanic acid, which was prepared according to the process as described in GB 1,508,977, with tert.butylamine in an organic solvent such as acetone, followed by the conversion of the isolated tert. butylamine salt of clavulanic acid to clavulanic acid or a pharmaceutically acceptable salt thereof.

SUMMARY OF THE INVENTION

The aim of the invention is to prepare clavulanic acid and pharmaceutically acceptable salts thereof, such as potassium salt, in a new and simple manner, thus obtaining the desired substance in a high yield and high purity by isolation from the concentrate of the extract, obtained in a known manner in an organic solvent after the fermentation with a clavulanic-acid-producing microorganism, wherein clavulanic acid is present in crude form.

This aim is achieved by conventionally treating the fermentation broth obtained after the fermentation with a clavulanic acid producing microorganism of the genus Streptomyces sp. P 6621 FERM P2804 as described in JP Kokai 80-162993 prior to the solvent extraction, which yields a solution of crude clavulanic acid in an organic solvent.

Solvents suitable for the extraction are ethyl acetate, methyl isobutyl ketone or butanol, the preferred one being ethyl acetate.

The organic phase is then washed with water and concentrated by evaporation to a crude clavulanic acid concentration of at least 20 g/l and to a residual water content of under 6 g/l. The obtained extract in the organic solvent, such as the ethyl acetate extract, is further subjected to a treatment with activated charcoal to eliminate any coloured matter.

The extract obtained in the above-described manner is reacted with substituted alkylenediamines of the formula II

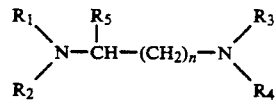

wherein the substituents $R_1$, $R_2$, $R_3$ and $R_4$ denote
  a hydrogen atom,
  a straight chain or a branched chain alkyl group having 1 to 8 carbon atoms,
  an arylalkyl group wherein the alkyl group is a methyl or ethyl group and the aryl group is a phenyl group, which is optionally para-substituted by a methyl, methoxy, nitro or halo (chloro or bromo) group, the aryl group on the alkyl chain being in α- or in β-position,
  a hydroxyalkyl group having 2 to 4 carbon atoms,
  an aminoalkyl group having 2 to 4 carbon atoms, which is optionally substituted by an N-alkyl or N,N-dialkyl group having 1 to 4 carbon atoms, or $R_1$ and $R_2$ or $R_3$ and $R_4$ jointly independently denote a cyclic alkylene ring having 3 to 6 methylene groups, one of these groups being optionally substituted by an oxygen or a sulphur atom or by an imino group and $R_5$ denotes a hydrogen atom, or a methyl group and n denotes an integer from 1 to 3, to yield alkylenediammonium diclavulanates of the formula I

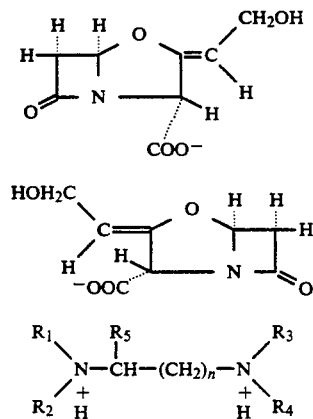

wherein the substituents have the above meanings. These salts are novel and have not yet been described in literature.

BEST AND VARIOUS MODES FOR CARRYING OUT INVENTION

The reactions are carried out most advantageously by using N,N'-monosubstituted symmetric ethylenediamines having an alkyl chain of medium length, wherein $R_1$ and $R_3$ denote an ethyl or an isopropyl group, $R_2$ and $R_4$ denote a hydrogen atom and n denotes 1.

As the most preferred alkylenediamine the N,N'-diisopropylethylenediamine is used, which yields the N,N'-diisopropyl-ethylenediammonium diclavulanate.

The alkylenediamine bases can be used either as such or, in the case that they are present in a solid form, in the form of solutions in organic solvents, such as acetone or ethyl acetate.

For the preparation of the salt of the clavulanic acid at least one equivalent of the selected alkylenediamine is used.

The desired salts of calvulanic acid (1:2) of the formula I, such as N,N'-diisopropylethylenediammonium diclavulanate, can then be isolated whereby the clavulanic acid is obtained free of most or even free of all impurities.

The desired salts of the clavulanic acid of the formula I are stable crystalline salts which excel by high purity, thus rendering a further purification by recrystallization unnecessary.

They are used as intermediate compounds for the preparation of pure clavulanic acid and pharmaceutically acceptable salts thereof, e.g. for the preparation of potassium clavulanate, whereat they are subjected to a double exchange by reaction with a carbonate, hydrogen carbonate or hydroxide of a pharmaceutically acceptable alkali metal or with a salt of an appropriate alkanoic acid, such as potassium 2-ethylhexanoate, in an organic solvent, such as isopropanol. In this reaction an ion exchange between the alkylenediammonium cation and the alkali metal cation takes place.

Another object of the present invention is a process for the purification of the clavulanic acid and of the pharmaceutically acceptable salts thereof, which is characterized in that crude clavulanic acid is reacted in an organic solvent with an appropriate substituted alkylenediamine of the formula II

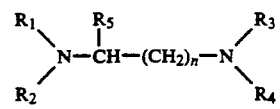

wherein the substituents $R_1$, $R_2$, $R_3$, $R_4$ and $R_5$ and n have the meanings as defined herein above, the obtained alkylenediammonium diclavulanate of the formula I

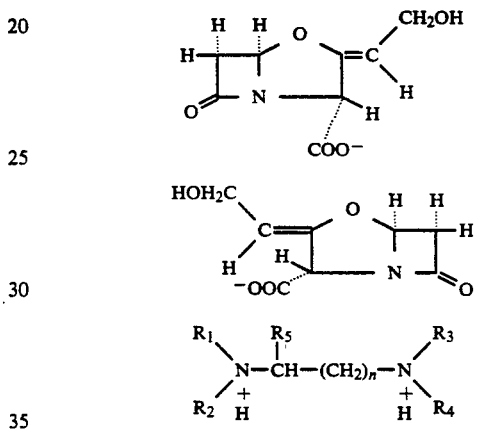

wherein the substituents $R_1$, $R_2$, $R_3$, $R_4$ and $R_5$ and n have the meanings as defined herein above, is optionally isolated and then coverted to the clavulanic acid or to the pharmaceutically acceptable salts thereof.

All steps of the process of the invention are carried out at temperatures about room temperature.

In comparison with the known method for the preparation of the clavulanic acid and pharmaceutically acceptable salts thereof as described in EP-0-026044, the process of this invention excels by the preparation of the intermediate product, i.e. of the salt of formula I in high yield and purity without any need of additional purification by recrystallization, and this intermediate product can be obtained directly from the ethyl acetate extract of the clavulanic acid without the use of additional organic solvents, such as acetone. According to the process as described in EP-0-026044 the clavulanate is precipitated with tert. butylamine, the obtained precipitate is treated with acetone, purified by reprecipitation with acetone from the isopropanol solution and then transformed in an isopropanolic solution to the potassium salt of the clavulanic acid.

The invention will be illustrated in more detail by the following, in no way limiting Examples.

PREPARATION OF STARTING MATERIALS

EXAMPLE 1

N,N'-diisopropylethylenediammonium diclavulanate

To the ethyl acetate extract obtained in accordance with known methods (1 l, crude clavulanic acid content 20 g/l, water content 6 g/l), which was previously partly discoloured by treatment with activated charcoal, N,N'-diisopropylethylenediamine (9 ml) was added under vigorous stirring within 10 min. The solution was stirred for another 30 min., whereat a precipitate separated. The obtained precipitate was dissolved in water (20 ml) diluted with acetone (400 ml), whereat N,N'-diisopropylethylenediammonium diclavulanate (13.0 g) separated in form of fine crystals, m.p. 130°–132° C.

$^1$H-NMR (D$_2$O, DSS, 300 Hz): δ = 1.33 (6H, d, J = 6.5 Hz, CH(CH$_3$)$_2$), 3.12 (1H, d, J = 17.0 Hz, 6-βCH), 3.38 (2H, s, NCH$_2$), 3.45 (1H, hept, J = 6.5 Hz, CHMe$_2$), 3.55 (1H, dd, J = 17.0 and 2.8 Hz, 6-αCH), 4.18 (1H, d, J = 7.4 Hz, CH', H"OH), 4.19 (1H, d, J = 7.8 Hz, CH'H"OH), 4.88–4.96 (2H, m, 3-CH, =CH-), 5.72 (1H, d, J = 2.8 Hz).

EXAMPLE 2

N,N'-diethylethylenediammonium diclavulanate

To the ethyl acetate extract obtained in accordance with known methods (1 l, crude clavulanic acid content 20 g/l, water content 6 g/l), which was previously partly discoloured by treatment with activated charcoal, were added acetone (2) and then under vigorous stirring within 15 min. N,N'-diethylethylenediamine (6.4 ml). The obtained mixture was stirred for another 30 min., the separated precipitate was filtered off and washed with acetone. The obtained amorphous precipitate was suspended in acetone (1 l,), broken up by vigorous stirring and the obtained suspension was filtered once again. The obtained product was dried, dissolved in water (20 ml) and the to the solution acetone (200 ml) was added. The clear fraction of the mixture was decanted from the soft mass adhering to the walls of the vessel and filtered. To the filtrate additional acetone (400 ml) was added whereat of a precipitate formed, which was filtered off and washed with acetone. Thus there was obtained the desired compound (10 g), m.p. 104°–108° C.

$^1$H-NMR (D$_2$O, DSS, 300 Hz): δ = 1.29 (3H, t, J = 7.3 Hz, CH$_2$CH$_3$), 3.11 (1H, d, J = 17.0 Hz, 6-βCH), 3.16 (2H, q, J = 7.3 Hz, CH$_2$CH$_3$), 3.41 (2H, s, NCH$_2$), 3.55 (1H, dd, J = 17.0 and 2.7 Hz, 6-αCH), 4.18 (1H, d, J = 8.2 Hz, CH', H"OH), 4.18 (1H, d, J = 8.0 Hz, CH'H"OH), 5.85–5.96 (2H, m, 3-CH, =CH-), 5.72 (1H, d, J = 2.7 Hz).

PROCESS ACCORDING TO THE INVENTION

EXAMPLE 3

Potassium clavulanate

N,N'-diisopropylethylenediammonium diclavulanate (10 g, clavulanic acid content 69%) was dissolved in water (10 ml), the solution was diluted with isopropanol (190 ml) and a solution (15 ml, 2M) of potassium 2-ethylhexanoate in isopropanol was added within 15 min. with stirring. The obtained suspension was stirred for another 30 min. whereat a precipitate separated, which was filtered off, washed with isopropanol and then dried. Thus there was obtained potassium clavulanate (4.8 g; 70%), (USP Grade, clavulanic acid content 81% as determined by the HPLC method).

EXAMPLE 4

Potassium clavulanate

N,N'-diethylethylenediammonium diclavulanate (10 g, clavulanic acid content 70%) was dissolved in water (10 ml) and to the resulting solution isopropanol (190 ml) was added. The mixture was filtered off and a solution of potassium 2-ethylhexanoate in isopropanol (15 ml, 2M) was added to the filtrate within 15 min. with stirring. The obtained suspension was stirred for another 30 min. whereat a precipitate formed, which was filtered off, washed with isopropanol and then dried. Thus there was obtained potassium clavulanate (4.0 g; 47%), (USP Grade, clavulanic acid content 81% as determined by the HPLC method).

I claim:

1. Alkylenediammonium diclavulanate of the formula I

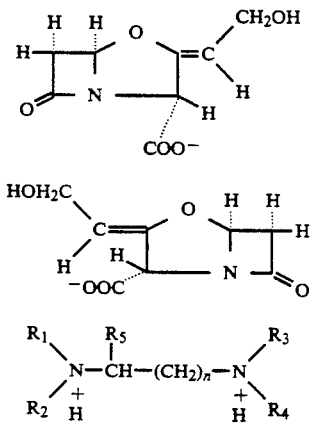

wherein the substituents R$_1$, R$_2$, R$_3$, and R$_4$ each individually denote
   a hydrogen atom,
   a straight chain or a branched chain alkyl group having 1 to 8 carbon atoms, or
   a hydroxyalkyl group having 2 to 4 carbon atoms, or
   NR$_1$R$_2$ or NR$_3$R$_4$ jointly denote a heterocyclic ring having 3 to 6 methylene groups attached to the nitrogen atom, one of these groups being optionally substituted by an oxygen or a sulfur atom or by an imino group,
   R$_5$ denotes a hydrogen atom or a methyl group, and n denotes an integer from 1 to 3.

2. N,N'-diisopropylethylenediammonium diclavulanate.

3. N,N'-diethylethylenediammonium diclavulanate.

4. The diclavulanate of claim 1 wherein R$_2$ and R$_4$ each denote a hydrogen atom and n denotes 1.

* * * * *

UNITED STATES PATENT AND TRADEMARK OFFICE
CERTIFICATE OF CORRECTION

PATENT NO. : 5,310,898
DATED : May 10, 1994
INVENTOR(S) : Copar

It is certified that error appears in the above-identified patent and that said Letters Patent is hereby corrected as shown below:

On the title page:Item
[75] Inventor:

Please delete "Spratly Islands"and insert ---Slovenia---

[73] Assignee:

Please delete "Spratly Islands" and insert ---Slovenia---

Signed and Sealed this

Sixth Day of September, 1994

Attest:

BRUCE LEHMAN

Attesting Officer     Commissioner of Patents and Trademarks